(12) United States Patent
Kiessling et al.

(10) Patent No.: US 9,006,394 B2
(45) Date of Patent: Apr. 14, 2015

(54) PEPTIDE-PRESENTING SURFACES FOR LONG-TERM CULTURE OF PLURIPOTENT CELLS

(71) Applicant: Wisconsin Alumni Research Foundation, Madison, WI (US)

(72) Inventors: Laura Lee Kiessling, Madison, WI (US); Joseph R. Klim, Boston, MA (US); Lingyin Li, Boston, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/162,539

(22) Filed: Jan. 23, 2014

(65) Prior Publication Data

US 2014/0287505 A1    Sep. 25, 2014

Related U.S. Application Data

(62) Division of application No. 12/563,009, filed on Sep. 18, 2009, now Pat. No. 8,648,170.

(60) Provisional application No. 61/098,703, filed on Sep. 19, 2008.

(51) Int. Cl.
| | |
|---|---|
| *C12N 5/074* | (2010.01) |
| *C12N 5/0735* | (2010.01) |
| *A61K 38/04* | (2006.01) |
| *A61K 38/10* | (2006.01) |
| *A61K 38/08* | (2006.01) |

(52) U.S. Cl.
CPC .............. *C12N 5/0696* (2013.01); *A61K 38/04* (2013.01); *A61K 38/08* (2013.01); *A61K 38/10* (2013.01); *C12N 5/0606* (2013.01); *C12N 2533/52* (2013.01); *C12N 2501/727* (2013.01); *C12N 2533/50* (2013.01)

(58) Field of Classification Search
None
See application file for complete search history.

(56) References Cited

U.S. PATENT DOCUMENTS

| | | | |
|---|---|---|---|
| 7,858,585 B2 | 12/2010 | Ozbas et al. | |
| 7,892,830 B2 | 2/2011 | Bergendahl et al. | |
| 8,062,890 B2 | 11/2011 | Kiessling et al. | |
| 8,501,905 B2 | 8/2013 | Schaffer et al. | |
| 2007/0026518 A1 | 2/2007 | Healy | |
| 2010/0068793 A1 | 3/2010 | Ungrin | |

FOREIGN PATENT DOCUMENTS

| | | |
|---|---|---|
| WO | 2004053096 A3 | 6/2004 |
| WO | 2004055155 A2 | 7/2004 |
| WO | 2006029198 A2 | 3/2006 |
| WO | 2008089351 A1 | 7/2008 |
| WO | 2008106771 A1 | 9/2008 |

OTHER PUBLICATIONS

Amit M, et al., "Feeder layer- and serum-free culture of human embryonic stem cells," Biol. Reprod. 70:837-845 (2004).
Amit M, et al., "Human feeder layers for human embryonic stem cells," Biol. Reprod. 68:2150-2156 (2003).
Anderson et al., Nanoliter-scale synthesis of arrayed biomaterials and application to human embryonic stem cells, Nat. Biotechnol. 22:863-866 (2004).
Ashton, R, et al., "Progress and prospects for stem cell engineering," Annu. Rev. Chem. Biomol. Eng. 2:479-502 (2011).
Braam S, et al., "Recombinant vitronectin is a functionally defined substrate that supports human embryonic stem cell self renewal via αVβ5 integrin," Stem Cells 2008; 26: 2257-2265 [Epub ahead of print, Jul. 17, 2008].
Cowan C, et al., "Nuclear reprogramming of somatic cells after fusion with human embryonic stem cells," Science 309:1369-1373 (2005).
Derda R, et al., "Defined substrates for human embryonic stem cell growth identified from surface arrays," ACS Chem. Biol. 2:347-355 (2007).
Derda R, et al., "Solid-phase synthesis of alkanethiols for the preparation of self-assembled monolayers," Langmuir 23:11164-11167 (2007).
Emami S, et al.: Self-renewal and proliferation of murine embryonic stem cells: A study of glycosaminoglycans effect on feeder-free cultures, May 2007, pp. 314-322, vol. 22, No. 3, Journal of Bioactive and Compatible Polymers.
Evans M & Kaufman M, "Establishment in culture of pluripotential cells from mouse embryos," Nature 292:154-156 (1981).
Falsey J, et al., "Peptide and small molecule microarray for high throughput cell adhesion and functional assays," Bioconjug. Chem. 12, 346-353 (2001).
Fromm J, et al., "Pattern and Spacing of Basic Amino Acids in the Heparin Binding Sites", Arch. Biochem. Biophys. 343:92-100 (1997).
Gerecht S, et al., "Hyaluronic acid hydrogel for controlled self-renewal and differentiation of human embryonic stem cells," Proc. Natl. Acad. Sci. USA 104:11298-11303 (2007).
Hoffman & Carpenter, "Characterization and culture of human embryonic stem cells," Nature Biotechnol. 23:699-708 (2005).
Houseman B & Mrksich M, "Efficient solid-phase synthesis of peptide-substituted alkanethiols for the preparation of substrates that support the adhesion of cells," J. Org. Chem. 63:7552-7555 (1998).
Imreh M, et al., "Culture and expansion of the human embryonic stem cell line HS181, evaluated in a double-color system," Stem Cells Dev. 13:337-343 (2004).
Jackson R, et al, "Glycosaminoglycans molecular properties protein interactions and role in physiological processes," Physiological Reviews, American Physiological Society, vol. 71, No. 2, pp. 481-539 (1991).
Jones D & Wagers A, "No place like home: anatomy and function of the stem cell niche" Stem Cells Reviews, 9:11-21 (2008).

(Continued)

*Primary Examiner* — Maury Audet
(74) *Attorney, Agent, or Firm* — Quarles & Brady LLP

(57) ABSTRACT

The present invention relates to methods of growing and maintaining pluripotent cells on an insoluble substrate that presents a peptide that binds to glycosaminoglycans, such as heparin. Specifically, methods of growing and maintaining pluripotent cells on substrates having a chemically defined surface presenting at least one peptide having basic amino acid residues separated by one or two hydrophobic amino acid residues.

5 Claims, 6 Drawing Sheets

(56) References Cited

OTHER PUBLICATIONS

Kaiser E, et al., "Color test for detection of free terminal amino groups in solid-phase synthesis of peptides," Anal. Biochem. 34:595-598 (1970).

Kyte J & Doolittle R, "A simple method for displaying the hydropathic character of a protein," J. Mol. Biol. 157:105-132 (1982).

Klein E, et al., "Cell adhesion, cellular tension, and cell cycle control," Meth. Enzymol. 426:155-175 (2007).

Klim, J, et al., "A defined glycosaminoglycan-binding substratum for human pluripotent stem cells," Nature Methods, 7 (12):989-994 (2010).

Lee J, et al., "Establishment and maintenance of human embryonic stem cell lines on human feeder cells derived from uterine endometrium under serum-free condition," Biol. Reprod. 72:42-49 (2005).

Ludwig T, et al., "Derivation of human embryonic stem cells in defined conditions," Nat. Biotechnol. 24:185-187 (2006).

Ludwig T, et al., "Feeder-independent culture of human embryonic stem cells," Nat. Methods 3:637-646 (2006).

McCarthy J, et al., "RGD-independent cell adhesion to the carboxy-terminal heparin-binding fragment of fibronectin involves heparin-dependent and -independent activities," J. Cell Biol. 110:777-787 (1990).

Orner et al., "Array for the Combinatorial Exploration of Cell Adhesion," J. Am. Chem. Soc. 126:10808-10809 (2004).

Thomson J, et al., "Embryonic stem cell lines derived from human blastocysts," Science 282:1145-1147 (1998).

Vogel B, et al., "A novel integrin specificity exemplified by binding of the alpha v beta 5 integrin to the basic domain of the HIV Tat protein and vitronectin," J. Cell Biol. 121:461-468 (1993).

Votteler, M, et al, "Stem cell microenvironments—unveiling the secret of how stem cell fate is defined," Macromolecular Bioscience, 10:1302-1315 (2010).

Watanabe K, et al., "A ROCK inhibitor permits survival of dissociated human embryonic stem cells," Nat. Biotechnol. 25:681-686 (2007).

Wilmut I, et al., "Viable offspring derived from fetal and adult mammalian cells," Nature 385:810-813(1997).

Xu C, et al., "Feeder-free growth of undifferentiated human embryonic stem cells," Nat. Biotechnol. 19:971-974 (2001).

Yu J, et al., "Human embryonic stem cells reprogram myeloid precursors following cell-cell fusion," Stem Cells 24:168-176 (2006).

Yu J, et al., "Induced pluripotent stem cell lines derived from human somatic cells," Science 318:1917-1920 (2007).

Non-patent literature cited during the examination procedure, PCT/US2009/057705, Jul. 7, 2011.

PCT Written Opinion and International Search Report, PCT/US2009/057705, May 27, 2010.

European Patent Office Examination Report, Patent Application No. 09737231.2, Jun. 27, 2014.

European Patent Office Examination Report, Patent Application No. 09737231.2, Jun. 28, 2012.

Australia Patent Office Examination Report, Patent Application No. 2009292972, Jul. 15, 2014.

Israel Patent Office Action, Patent Application No. 211749, May 12, 2013.

Japan Patent Office Action, Patent Application No. 2011-0528041, Mar. 14, 2014.

Singapore Patent Office Written Opinion and Search Report, Patent Application No. 2011019874, May 10, 2012.

Bendall, et al. "IGF and FGF cooperatively establish the regulatory stem cell niche of pluripotent human cells in vitro." Nature (2007) 448:1015-1021 (2007).

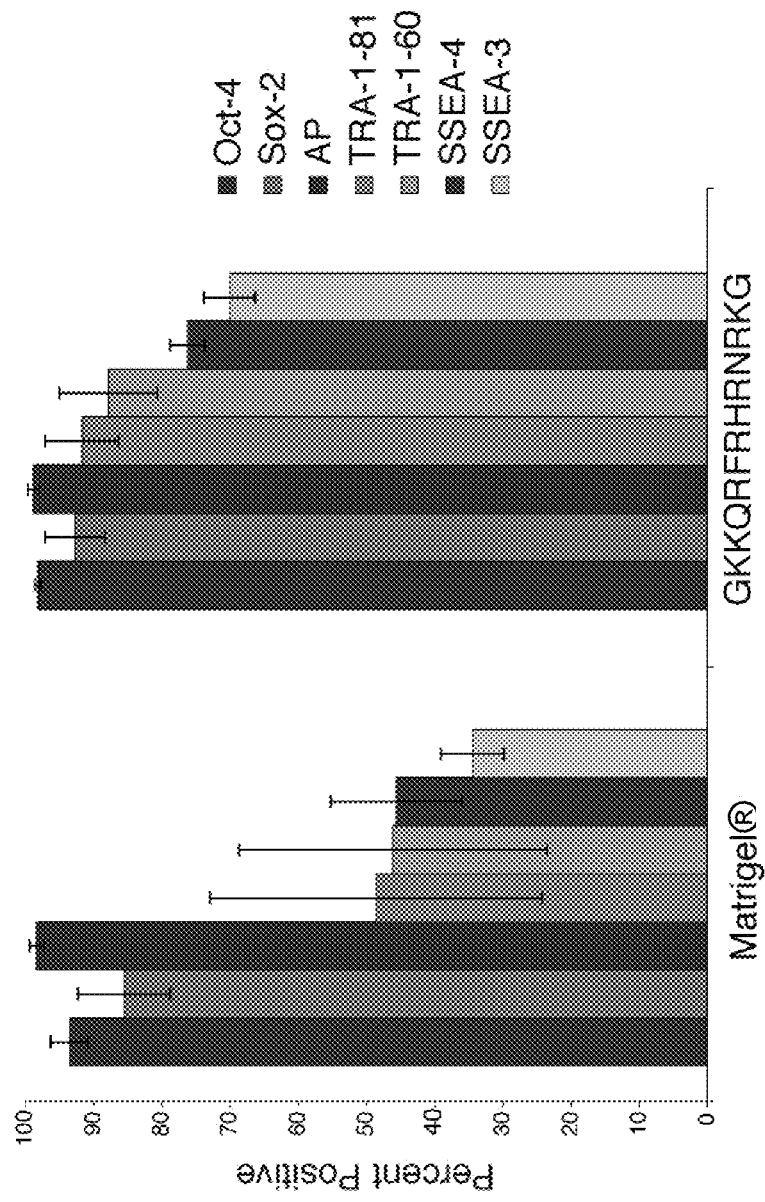

Sequences of Selected Heparin Binding Sites

| Protein | SEQ ID NO: | Peptide sequences | Criteria |
|---|---|---|---|
| bFGF (27) | 10 | ¹²⁸TTFERLESNNYNTYRSRKYSSWYVALKR¹⁵⁵ | a |
| Antithrin (28) | 11 | ²⁸⁶KGLRRLJACEYKTERPKRRLJRRLS³⁰⁴ | a |
| Apo E (29) | 12 | ¹⁴²LRKRLLR¹⁴⁸ | a |
| | 13 | ²²³GERLRAR²²⁹ | a |
| LPL (30, 31) | 14 | ²⁷⁹RKNRCVLGTEHKVRAKR²⁹⁵ | a |
| EC-SOD (32) | 15 | ²¹⁰REHSERKKRRESECKAA²²⁶ | a |
| vWF (33) | 16 | ⁵⁶⁵YIGLKDRKRPSELRRIASQVKYA⁵⁸⁷ | a |
| NCAM (34) | 17 | ¹⁸TWKKAPDYTLKDRF³¹ | a |
| Fibronectin (35–37) | 18 | ¹RKARVTDATETTITISWRTKTETITGFQVDAIPANG³⁴ | a |
| | 19 | ⁵⁰⁷YEKPGSPPREVVPRPRPGV⁵²⁵ | a |
| | 20 | ¹⁷²⁰QSSQSEPLIGRKKT¹⁷³³ | a |
| Laminin (38, 39) | 21 | ⁵⁶³RYVVLPRPVCFEKGMNYTVR⁵⁸² | a |
| | 22 | ²⁷²⁵RIQNLLKIIDLRIKFVK²⁷⁴¹ | a |
| | 23 | ³⁰⁰³QPNCLLSSRSCFYGRGVSR³⁰²¹ | a,c |
| | 24 | ²⁰²⁵AKKQRFRHRNRSCR²⁰³⁸ | a |
| Vitronectin (40) | 25 | ³⁴⁸AKLNCRLYRRANSKLYSAAR³⁶⁷ | a |
| ATIII (41–43) | 26 | ⁴¹KGGRRTLDLQAPLVKFLKELLS⁶² | a |
| PF4 (44, 45) | 27 | ⁵⁵CRCRRRTCYY⁶³ | a |
| Lpp-C channel (46) | 28 | MCRMKRYA | a |
| bFGF (45–50) | 29 | ¹¹⁸RKHAERWPVGLKKNGSCKRG¹³⁷ | a |
| Protein C inhibitor (51, 52) | 30 | ²⁶⁴SEKTLRKWLKMFKRQLE³⁸² | a |
| 800 kDa stress protein (53) | 31 | ⁸⁰⁷LYNK⁸⁰¹⁰ | a,c |
|   | 32 | ¹⁷¹¹LRKC¹⁷¹⁴ | a,c |
| Thrombospondin (54–56) | 33 | ²⁵RKSSGRRLYK⁶⁵ | a |
|   | 34 | ¹⁰³GRRTR⁶⁹ | a |
| TGF β (57) | 35 | ⁴¹DRRELGWKRHEPRCGYTAA⁴⁷⁸ | a |
| Apo B100 (58) | 36 | ²⁹⁹LSVPAQYTKKNNKHSHS³¹⁵ | a |
|   | 37 | ³³⁴⁶YRLEGYTLRLTRKRGLKLAT A³³⁶⁵ | a |
|   | 38 | ³⁵⁴⁵CRPRHSKKRKKKRLKQR³⁵⁶⁰ | a |
|   | 39 | ⁴²⁷²LGVPAMRIVRKKRKR⁴²⁸⁶ | a |
| PDGF-A (59, 60) | 40 | ²¹⁰KKKAPKVQKKRKKA²¹⁷ | a |
| Xanthine oxidase (61) | 41 | ²¹⁰RYVNQVGRVLKKIDKAIVSKRNK³¹² | a |
| Gla derived protein (62) | 42 | ¹²QKCSPFYYSGCGGNSNVFYTSKQECLRACKX⁴² | a |
| TFPI (63) | 43 | ²⁵⁴KRKRKKE²⁶⁰ | a |
| AAMP (64) | 44 | ²⁰³⁸RKGFYRRCGPSRGHKR²¹³ | a |
| IGBP-3 (65) | 45 | ²²⁰KKGFYRRKQCRPSKGRKR²³⁶ | a,b |
| HB-EGF (67) | 46 | ²¹²RKKKGKCGLGKKKDRF⁶⁷ | a,b |

PEPTIDE-PRESENTING SURFACES FOR LONG-TERM CULTURE OF PLURIPOTENT CELLS

CROSS-REFERENCE TO RELATED APPLICATIONS

This application is a divisional application of U.S. application Ser. No. 12/563,009, filed Sep. 18, 2009, which claims the benefit of U.S. Provisional Patent Application No. 61/098,703, filed Sep. 19, 2008, each of which is incorporated herein by reference as if set forth in its entirety.

STATEMENT REGARDING FEDERALLY SPONSORED RESEARCH OR DEVELOPMENT

This invention was made with government support under AI055258 awarded by the National Institutes of Health. The government has certain rights in the invention.

BACKGROUND

The invention relates generally to culturing pluripotent cells, and more particularly to chemically defined (i.e., synthetic) surfaces for long-term growth and maintenance (i.e., self-renewal) of pluripotent cells.

Pluripotent cells, such as embryonic stem cells (ESCs) and induced pluripotent stem cells (iPS cells), have at least two characteristics that distinguish them from other types of cells. The first characteristic is that they are self-renewing, and thus are capable of growing indefinitely without differentiating. The second characteristic is that they can differentiate into cells of all three germ layers (i.e., endoderm, mesoderm, and ectoderm). See, e.g., Evans M & Kaufman M, "Establishment in culture of pluripotential cells from mouse embryos," Nature 292:154-156 (1981), incorporated herein by reference as if set forth in its entirety.

One difficulty in working with pluripotent cells is developing standardized culture conditions for these cells without requiring the use of animal products or products such as serum, which tend to vary from batch to batch, to maintain the characteristics noted above. Important aspects of culturing these cells, therefore, are not only the medium in which they are grown, but also the surface upon which they are cultured.

Of particular interest herein are surfaces for culturing pluripotent cells, as these cells require adhesion/attachment to a surface to maintain the characteristics noted above. Although much information is available on chemically defining the constituents for culture medium for these cells, considerably less information is available on chemically defining the constituents of the surfaces and cell-substrate attachment for their survival and growth.

Initially, pluripotent cells were cultured on gelatin-coated surfaces containing mouse embryonic fibroblasts (MEFs) or other feeder cells. See, e.g., Amit M, et al., "Human feeder layers for human embryonic stem cells," Biol. Reprod. 68:2150-2156 (2003); Lee J, et al., "Establishment and maintenance of human embryonic stem cell lines on human feeder cells derived from uterine endometrium under serum-free condition," Biol. Reprod. 72:42-49 (2005); and Thomson J, et al., "Embryonic stem cell lines derived from human blastocysts," Science 282:1145-1147 (1998). Pluripotent cells, however, do not grow on top of feeder cells, but instead tend to occupy the exposed gelatin-coated surface. As the cells proliferate, the growing colony pushes the MEFs away. See, e.g., Imreh M, et al., "Culture and expansion of the human embryonic stem cell line HS181, evaluated in a double-color system," Stem Cells Dev. 13:337-343 (2004).

The art recognized that pluripotent cells can be cultured on a gelatin-coated surface in the presence of secreted factors from feeder cells, allowing the cells to be cultured in the absence of feeder cell layers (i.e., feeder-free). For example, feeder cell layers can be avoided through the use of "conditioned medium" (CM), which is medium in which feeder cells were cultured. However, culture of pluripotent cells on gelatin-coated surfaces in CM can lead to rapid differentiation of the cells. See, e.g., Xu C, et al., "Feeder-free growth of undifferentiated human embryonic stem cells," Nat. Biotechnol. 19:971-974 (2001).

More recently, the art recognized that feeder cell layers also can be avoided by using a chemically defined culture medium (i.e., a complete medium), in which each constituent of the medium is fully disclosed and characterized. See, e.g., Ludwig T, et al., "Feeder-independent culture of human embryonic stem cells," Nat. Methods 3:637-646 (2006); and Ludwig T, et al., "Derivation of human embryonic stem cells in defined conditions," Nat. Biotechnol. 24:185-187 (2006), each of which is incorporated herein by reference as if set forth in its entirety.

One should not, however, overlook the role of surface attachment for successful pluripotent cell maintenance and growth. In this regard, feeder cell layers can be avoided through the use of a commercially produced extracellular matrix (ECM) material, such as Matrigel®. Matrigel®, however, contains indeterminate (i.e., undefined) quantities of murine extracellular matrix proteins, such as laminin, collagen and entactin. Additionally, there is batch to batch variation within Matrigel® and other unknown components such as, growth factors. Other ECM materials that can be used for pluripotent cell culture include vitronectin, fibronectin and laminin.

Chemically defined surfaces for pluripotent cells have been described (see, e.g., Derda R, et al., "Defined substrates for human embryonic stem cell growth identified from surface arrays," ACS Chem. Biol. 2:347-355 (2007); and Gerecht S, et al., "Hyaluronic acid hydrogel for controlled self-renewal and differentiation of human embryonic stem cells," Proc. Natl. Acad. Sci. USA 104:11298-11303 (2007), but these surfaces have not yet proven effective for long-term growth and maintenance of pluripotent cells. Specifically, cells grown on these surfaces for several weeks form heterogeneous cell populations of undifferentiated and differentiated cells, which can be challenging to separate from one another. Bendall et al. "IGF and FGF cooperatively establish the regulatory stem cell niche of pluripotent human cells in vitro." Nature (2007) 448:1015-1021 (2007). In addition, these surfaces typically rely on ECM proteins from animal or human sources. See, e.g., Amit M, et al., "Feeder layer- and serum-free culture of human embryonic stem cells," Biol. Reprod. 70:837-845 (2004); Braam S, et al., "Recombinant vitronectin is a functionally defined substrate that supports human embryonic stem cell self renewal via αVβ5 integrin," Stem Cells [Epub ahead of print, Jul. 17, 2008]; and Xu et al., supra.

As such, the art desires insoluble substrates with chemically defined surfaces and culture conditions for pluripotent cells that support their long-term growth and maintenance.

Further, there is a great need for methods for differentiating pluripotent cells on defined substrates and separating the differentiated cells from undifferentiated pluripotent cells.

BRIEF SUMMARY

In a first aspect, the present invention is summarized as an insoluble substrate that presents a peptide that binds to a glycosaminoglycan (GAG). In one embodiment, the substrate has a chemically defined surface that presents a GAG-binding peptide that includes positively charged amino acid residues or basic (i.e., hydrophilic) amino acid residues separated by one or two hydrophobic amino acid residues (i.e., XZX, wherein X can be independently lysine, arginine or histidine and Z can be isoleucine, valine, leucine, phenalalanine, proline, methionine or alanine, and SEQ ID NO: 48, respectively), where the peptide occupies an area between about 0.5% to about 100%, about 0.5% to about 50%, about 1% to about 5% or about 1% of the peptide-presenting surface. In one embodiment, the peptide occupies an area that is at least 30% of the surface. The peptide can contain a GAG-binding motif and can be a synthetic peptide or a GAG-binding peptide portion of a longer polypeptide. A suitable peptide, without limitation, can range in length at least between about 3 and about 35 amino acids. A preferred peptide can range in length between about 7 and about 18 amino acids. A four amino acid GAG-binding peptide is described in the paper by Fromm, infra. The substrate having the chemically defined surface is suitable for long-term culture of pluripotent cells.

In a second aspect, the present invention is summarized as a cell culture vessel that includes a chemically defined surface that presents a peptide that includes positively charged amino acid residues or basic (i.e., hydrophilic) amino acid residues separated by one or two hydrophobic amino acid residues, where the peptide occupies an area between about 0.5% to about 25%, about 1% to about 5% or about 1% of the peptide-presenting surface. The culture vessel can also include a chemically defined medium that contains an effective amount of a kinase inhibitor.

In a third aspect, the present invention is summarized as a cell culture method that includes the step of culturing pluripotent cells on a surface as defined above.

In a fourth aspect, the present invention is summarized as a method for separating differentiated from undifferentiated cells that includes the step of culturing pluripotent cells on a surface as defined above, inducing differentiation, and separating differentiated from undifferentiated cells.

In a fifth aspect, the present invention is summarized as a composition having a surface presenting GAG-binding peptides as defined above and pluripotent stem cells adhering to the surface, wherein the cells display a normal karyotype, pluripotent cell-specific markers, and an ability to differentiate into all three germ layers after more than three months of culture on the surface.

In some embodiments, the chemically defined, peptide-presenting surface can include a self-assembled monolayer that includes one or more long-chain alkanethiol (AT) having, e.g., a structure of $X(CH_2)_nSH$, where n is between about 3 and about 50. In a preferred embodiment, n is between about 11 and about 18.

In some embodiments, the peptide can be a GAG-binding peptide (GBP), such as the heparin-binding domain from vitronectin (GKKQRFRHRNRKG; SEQ ID NO:1), from fibronectin (GWQPPRARI; SEQ ID NO:2) or from bone sialoprotein (FHRRIKA; SEQ ID NO:3).

In some embodiments, the kinase inhibitor can be a Rho-associated kinase (ROCK) inhibitor, such as Y-27632 [(+)-(R)-trans-4-(1-aminoethyl)-N-(4-pyridyl) cyclohexanecarboxamide dihydrochloride], H-1152 [(S)-(+)-(2-methyl-5-isoquinolinyl) sulfonylhomopiperazine], and HA-100 [1-(5-isoquinolinesulfonyl)piperazine hydrochloride].

The chemically defined surfaces can be used for growth and maintenance of pluripotent cells. Even after long-term (i.e., >3 months) culture on these surfaces, pluripotent cells retain a normal karyotype, pluripotent cell-specific markers characteristic of pluripotent cells and an ability to differentiate into all three germ layers (e.g., endoderm, mesoderm and ectoderm). In addition, these surfaces can display combinations of adhesive ligands/epitopes with control over ligand/epitope density, location and composition. These surfaces also minimize the exposure of pluripotent cells to potentially hazardous contaminants and/or animal products.

These and other features, objects and advantages of the present invention will become better understood from the description that follows. The description of preferred embodiments is not intended to limit the invention or to cover all modifications, equivalents and alternatives. Reference should therefore be made to the claims herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 1A shows a representative array presenting bioactive peptides and surface densities, which are reported as the percentage of peptide-ATs in a mixed SAM. Human ESCs (hESCs) bound to the surface in a peptide-specific and peptide-density dependent manner. Over 6 days, cells proliferated to fill the array elements (FIGS. 1B-G; higher magnification image of cells on the array stained for Oct-4 and SSEA-4 and counterstained with DAPI). FIG. 1B shows hESCs grown on a surface presenting a GBP derived from vitronectin (GKKQRFRHRNRKG; SEQ ID NO:1). FIG. 1C shows hESCs grown on a surface presenting a GBP derived from fibronectin (GWQPPRARI; SEQ ID NO:2). FIG. 1D shows hESCs grown on a surface presenting a GBP derived from bone sialoprotein (FHRRIKA; SEQ ID NO:3). FIG. 1E shows hESCs grown on a surface presenting a FGF receptor binding peptide (GGGEVYVVAENQQGKSKA; SEQ ID NO:4) and an integrin-binding peptide (KGRGDS; SEQ ID NO:5). FIG. 1F shows hESCs grown on a surface presenting the integrin-binding peptide (KGRGDS; SEQ ID NO:5) and another bioactive peptide derived from fibronectin (KPHSRN; SEQ ID NO:6). FIG. 1G shows hESCs grown on a surface presenting a laminin-derived bioactive peptide (GSDPGYIGSR; SEQ ID NO:7).

FIG. 2A shows that soluble heparin can abrogate hESC binding to surfaces coated with the heparin-binding peptide GKKQRFRHRNRKG (SEQ ID NO: 1), but not to surfaces coated with Matrigel or vitronectin. Percentages of cell binding represent the ratio of the mean luminescence of cell lysates prepared from cells plated in the presence of heparin versus those without heparin. The error bars indicate the standard deviation. FIG. 2B shows that hESCs cultured for 3 passages on SAMs presenting GBPs or a combination of the vitronectin GBP (GKKQRFRHRNRKG; SEQ ID NO:1) and the integrin-binding peptide (KGRGDS; SEQ ID NO:5) maintained pluripotent cell-specific marker expression (Oct-4, SSEA-3, and SSEA-4; SSEA-1 served as a marker of differentiation). Cells cultured on SAMs presenting the integrin-binding RGD peptide (KGRGDS; SEQ ID NO:5) alone, however, had significantly lower levels of pluripotent cell-specific markers after 3 passages. Cells also grew much more slowly on RGD-presenting surfaces than on surfaces presenting a GAG-binding peptide.

FIGS. 3A-3B show that synthetic surfaces presenting the vitronectin GBP (GKKQRFRHRNRKG; SEQ ID NO:1) support pluripotency and karyotype stability of hESCs over 3 months of culture. FIG. 3A shows that hESCs cultured on chemically defined surfaces for 3 months maintained high levels of markers of pluripotency. Error bars represent an average from 3 consecutive passages after passage 17. FIG. 3B shows that hESCs (H9 hESCs) cultured on vitronectin GBP (GKKQRFRHRNRKG; SEQ ID NO:1) for about 3 months were karyotypically normal as determined by standard G banding.

FIG. 4 shows a list of heparin-binding peptide sequences.

Figure 1:
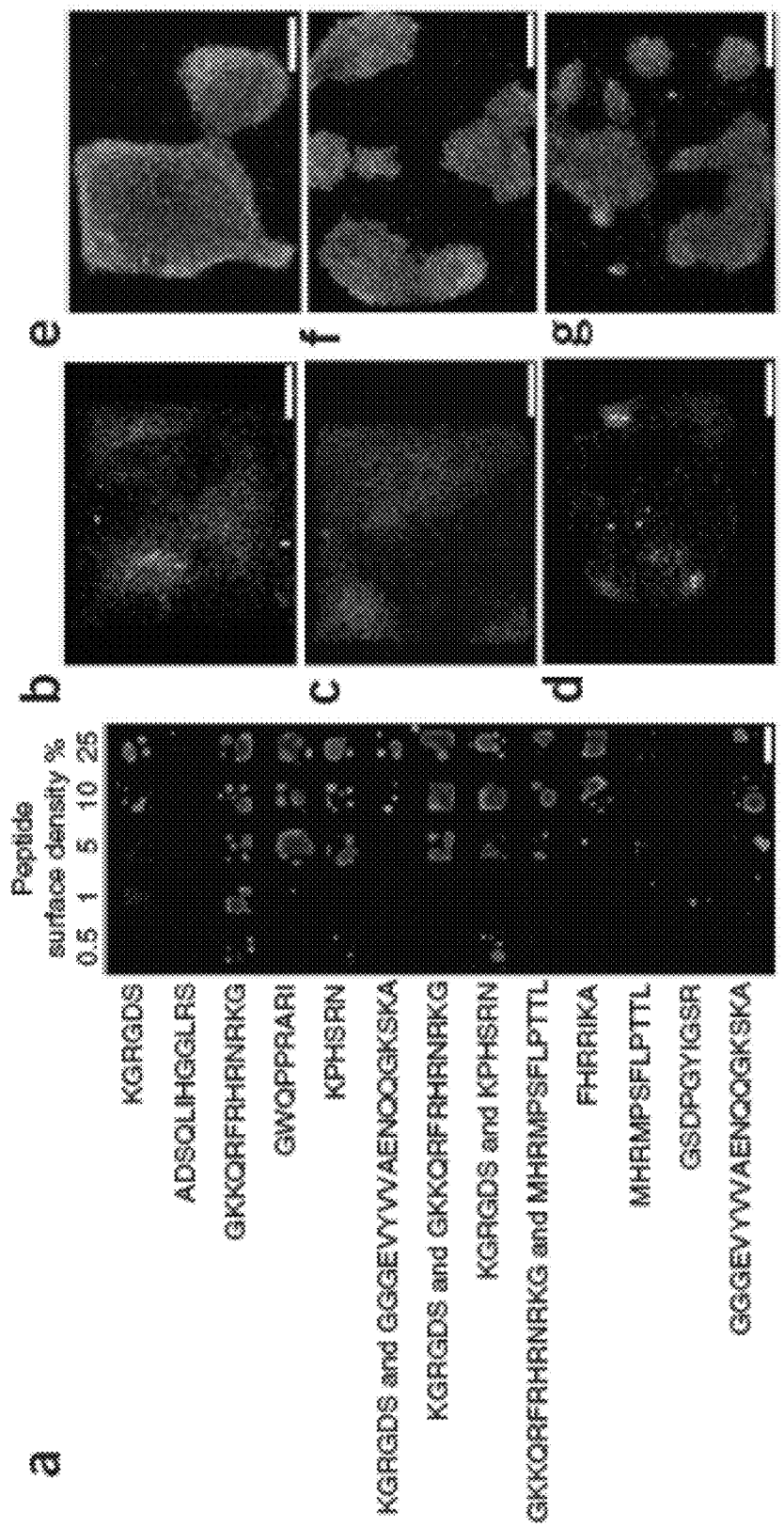
FIG. 1 shows the effects on pluripotent cell growth and maintenance of various peptides spotted onto a peptide-AT array in a mixed self-assembling monolayer (SAM).

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DESCRIPTION OF EXEMPLARY EMBODIMENTS

The present invention relates to the inventors' observation that pluripotent cells have cell surface receptors that recognize and adhere to GBPs, such as the heparin-binding peptide from vitronectin (i.e., GKKQRFRHRNRKG; SEQ ID NO:1). The inventors' therefore hypothesized that GBPs can be displayed on a surface as a synthetic alternative to a host of extracellular matrix proteins, such as those present in Matrigel®.

As described below, insoluble substrates with chemically defined surfaces presenting GBPs supported both pluripotent cell attachment and self-renewal, as assessed by the presence of Oct-4 and SSEA-4 after 6 days of culture. Although certain GBPs are known to promote cell adhesion and spreading, they have not been previously shown to support pluripotent cell self-renewal. See, e.g., McCarthy J, et al., "RGD-independent cell adhesion to the carboxy-terminal heparin-binding fragment of fibronectin involves heparin-dependent and -independent activities," J. Cell Biol. 110:777-787 (1990); and Vogel B, et al., "A novel integrin specificity exemplified by binding of the alpha v beta 5 integrin to the basic domain of the HIV Tat protein and vitronectin," J. Cell Biol. 121:461-468 (1993), each of which is incorporated herein by reference as if set forth in its entirety.

The chemically defined, peptide-presenting surfaces described herein are useful in a variety of contexts and applications. For example, the surfaces can be used for maintaining pluripotent cells in an undifferentiated state. In addition, the surfaces can be used for expanding a population of pluripotent, yet undifferentiated, cells. The chemically defined, peptide-presenting surfaces are also useful for culturing pluripotent cells that are subsequently induced to differentiate by, for example, adding one or more differentiation agent to the media. Differentiated cells derived from pluripotent cells can be maintained on the chemically defined surfaces.

Cell types pass through various levels of potency during differentiation, such as totipotency, pluripotency and multipotency. Of particular interest herein are pluripotent cells. As used herein, a "pluripotent cell" or "pluripotent cells" means a cell or population of cells that can differentiate into all three germ layers (e.g., endoderm, mesoderm, and ectoderm). Pluripotent cells express a variety of pluripotent cell-specific markers (e.g., Oct-4, SSEA-3, SSEA-4, Tra-1-60, or Tra-1-81, but not SSEA-1), have a cell morphology characteristic of undifferentiated cells (e.g., compact colony, high nucleus to cytoplasm ratio and prominent nucleolus) and form teratomas when introduced into an immunocompromised animal, such as a SCID mouse. See, e.g., Evans & Kaufman, supra. The teratomas typically contain cells or tissues characteristic of all three germ layers. One can assess these characteristics by using assays commonly used in the art. See, e.g., Thomson J, et al., "Embryonic stem cell lines derived from human blastocysts," Science 282:1145-1147 (1998), incorporated herein by reference as if set forth in its entirety.

Pluripotent cells are capable of proliferating in cell culture and differentiating towards a variety of lineage-restricted cell populations that exhibit multipotent properties. Pluripotent cells have a higher potency than multipotent cells, which are somatic cells that are more differentiated relative to pluripotent cells, but are not yet terminally differentiated.

Suitable pluripotent cells for use herein include ESCs and iPS cells, which preferably are from a primate, especially a human primate. As used herein, "embryonic stem cells" or "ESCs" mean a pluripotent cell or population of pluripotent cells derived from an inner cell mass of a blastocyst. See, Thomson et al., supra. These cells express at least Oct-4, SSEA-3, SSEA-4, TRA-1-60 or TRA-1-81, and appear as compact colonies having a high nucleus to cytoplasm ratio and prominent nucleolus. ESCs are commercially available from sources such as WiCell Research Institute (Madison, Wis.).

As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu J, et al., "Induced pluripotent stem cell lines derived from human somatic cells," Science 318:1917-1920 (2007), incorporated herein by reference as if set forth in its entirety.

iPS cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60 or Tra-1-81, but not SSEA-1). iPS cells, however, are not immediately derived from embryos. As used herein, "not immediately derived from embryos" means that the starting cell type for producing iPS cells is a non-pluripotent cell, such as a multipotent cell or terminally differentiated cell, such as somatic cells obtained from a post-natal individual.

Other types of pluripotent cells suitable for use herein include, but are not limited to, cells from somatic cell nuclear transfer (see, e.g., Wilmut I, et al., "Viable offspring derived from fetal and adult mammalian cells," Nature 385:810-813 (1997)) or cells from fusion of somatic cells with ESCs (see, e.g., Cowan C, et al., "Nuclear reprogramming of somatic cells after fusion with human embryonic stem cells," Science 309:1369-1373 (2005); and Yu et al., "Human embryonic stem cells reprogram myeloid precursors following cell-cell fusion," Stem Cells 24:168-176 (2006)).

Regardless of the pluripotent cell used, the chemically defined surfaces described herein can be constructed according to known methods. For example, one can use contact spotting of peptides onto glyoxylyl-functionalized glass slides (see, e.g., Falsey J, et al., "Peptide and small molecule microarray for high throughput cell adhesion and functional assays," Bioconjug. Chem. 12, 346-353 (2001)); contact printing of peptides onto acrylamide-coated glass slides; and spotting combinations of peptides onto a glass slide followed by in situ polymerization (see, e.g., Anderson et al., Nano-liter-scale synthesis of arrayed biomaterials and application to human embryonic stem cells, Nat. Biotechnol. 22:863 (2004). In addition, one can use streptavidin-coated plates treated with a biotinylated peptide of interest or even polyacrylamide gels cross-linked to a peptide of interest. See, e.g., Klein et al., Cell adhesion, cellular tension, and cell cycle control, Meth. Enzymol. 426:155 (2007). Water-insoluble synthetic or natural hydrogels are also contemplated as providing a suitable peptide-presenting surface.

As used herein, a "glycosaminoglycan" (GAG)" is a polysaccharide composed of repeating disaccharide units and amino sugars. Glycosaminoglycans are negatively charged and can be linked to proteins to form proteoglycans. Examples of glycosaminoglycans include chondroitin sulfate, dermatan sulfate, heparin, heparan sulfate, hyaluronate, and keratan sulfate.

Preferably, one spots ATs onto an inert background to form self-assembling monolayers (SAMs). See, e.g., Derda et al., supra; Derda R, et al., "Solid-phase synthesis of alkanethiols for the preparation of self-assembled monolayers," Langmuir 23:11164-11167 (2007); and Houseman B & Mrksich M, "Efficient solid-phase synthesis of peptide-substituted alkanethiols for the preparation of substrates that support the adhesion of cells," J. Org. Chem. 63:7552-7555 (1998), each of which is incorporated herein by reference as if set forth in its entirety. For example, a background can be formed of perfluoro-AT, which can be both cytophobic (i.e., repel cells) and solvophobic (i.e., repel solvents). First, a gold-coated surface can be coated with a perfluoro-AT monolayer, either leaving areas (i.e., holes) in the monolayer for the elements of an array or creating areas in the monolayer for the elements of the array in a subsequent step. Then, ATs coupled to a peptide, such as an GBP as described herein, can be attached to the substrate in the holes to complete the monolayer and to present ligands for pluripotent cell attachment to the surface. Surface density of the GBPs can be controlled using mixed SAMs of peptide-ATs and non-adhesive glucamine-ATs. Methods for synthesizing the AT species for both regions on the chemically defined surface array are provided in the examples below. For long-term culture on gold-coated coverslips (as opposed to array elements), a mixed monolayer of peptide-AT and glucamine-AT (5% peptide-AT) was formed. After 24 hours, the surfaces were washed with ethanol and cells were plated on the surfaces.

Figure 5:
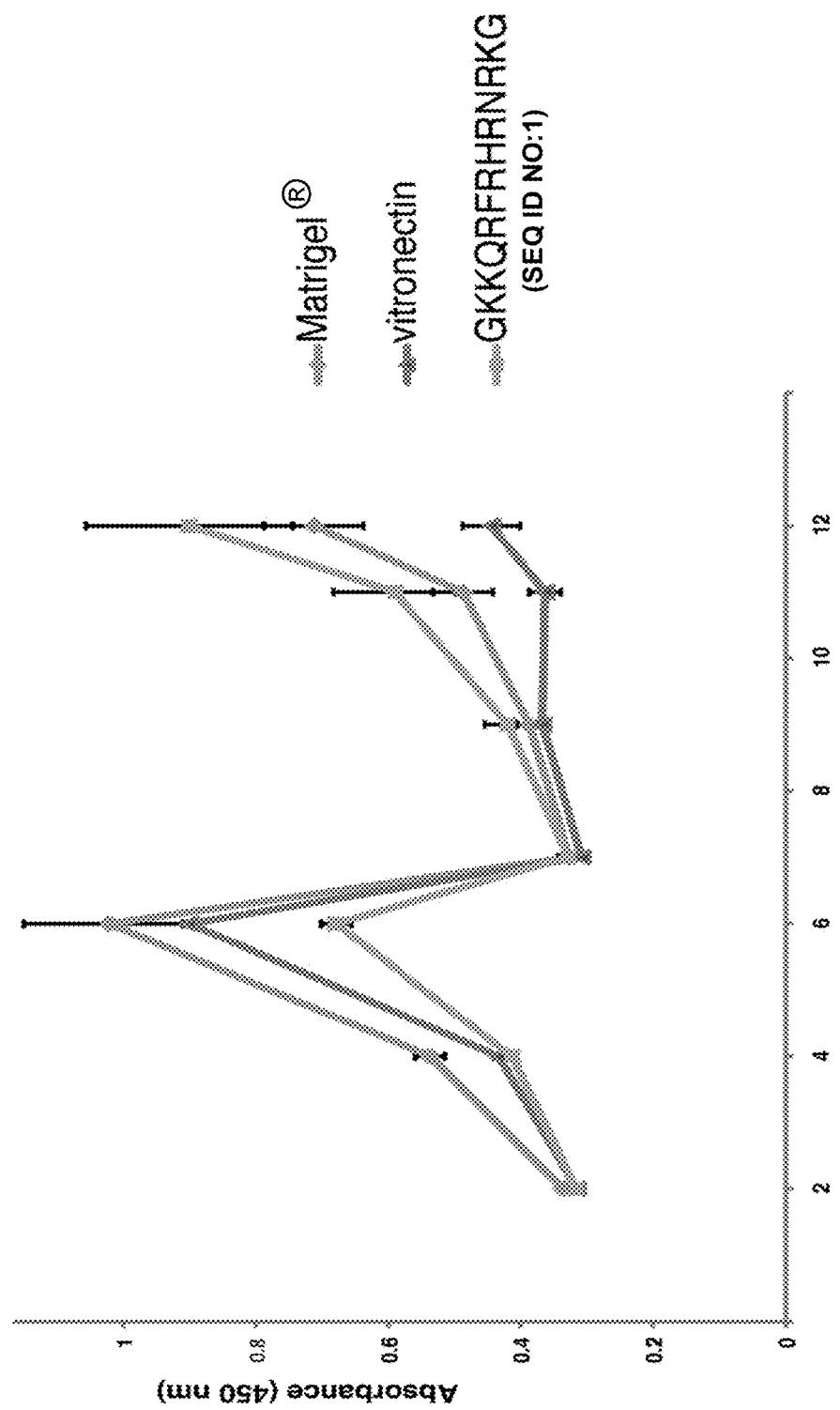
FIG. 5 shows growth characteristics of hESCs cultured on natural and synthetic substrates.

Each AT species may be thought of as having three important regions or moieties. One region is at the basal end, which is an attachment moiety intended to attach the monolayer species to the surface. The attachment moiety is typically a thiol group, which attaches to the gold substrate. Other attachment groups can attach to other substrates. Another region is the intermediate region, which is a spacer moiety, such as an alkane of between about 3 and about 50 carbons in length, and preferably between about 11 and about 18 carbons in length, as described elsewhere in this application. Other simple organic groups can be used for the spacer as long as the resulting species are capable of self-assembly in a monolayer. Lastly, the active group at the end of the monolayer species is the ligand, which can be a group intended to be cytophobic or cytophilic. Cytophilic ligands suitable for use herein include, but are not limited to, a peptide, especially a peptide having basic amino acid residues separated by one or two hydrophobic amino acid residues, like the vitronectin GBP (SEQ ID NO:1), fibronectin GBP (SEQ ID NO:2) and bone sialoprotein GBP (SEQ ID NO:3). As shown in FIG. 5, not all GBP sequences possess basic amino acid residues separated by one or two hydrophobic amino acid residues. Indeed, the inventors predict that if a peptide binds a gycosaminoglycan, it is capable of self renewing pluripotent stem cells.

Basic (i.e., hydrophilic) amino acids are polar and positively charged at pH values below their pKa's. Examples of basic amino acids include lysine, histidine and arginine.

The hydropathy index of an amino acid is a number representing the hydrophobic or hydrophilic properties of its side-chain. See, Kyte J & Doolittle R, "A simple method for displaying the hydropathic character of a protein," J. Mol. Biol. 157:105-132 (1982). The larger the number is, the more hydrophobic the amino acid. The most hydrophobic amino acids are isoleucine (4.5) and valine (4.2); whereas the most hydrophilic ones are arginine (−4.5) and lysine (−3.9). Hydropathy is important in protein structure, as hydrophobic amino acids tend to be internal (with regard to the protein's three-dimensional shape), while hydrophilic amino acids are more commonly found towards the protein's surface.

TABLE 1

Hydropathy index for the twenty natural amino acids (Kyte & Doolittle).

| A | R | N | D | C | Q | E | G | H | I | L | K | M | F | P | S | T | W | Y | V |
|---|---|---|---|---|---|---|---|---|---|---|---|---|---|---|---|---|---|---|---|
| 1.8 | −4.5 | −3.5 | −3.5 | 2.5 | −3.5 | −3.5 | −0.4 | −3.2 | 4.5 | 3.8 | −3.9 | 1.9 | 2.8 | −1.6 | −0.8 | −0.7 | −0.9 | −1.3 | 4.2 |

TABLE 2

Amino acids sorted by increasing hydropathy index.

| R | K | N | D | Q | E | H | P | Y | W | S | T | G | A | M | C | F | L | V | I |
|---|---|---|---|---|---|---|---|---|---|---|---|---|---|---|---|---|---|---|---|
| −4.5 | −3.9 | −3.5 | −3.5 | −3.5 | −3.5 | −3.2 | −1.6 | −1.3 | −0.9 | −0.8 | −0.7 | −0.4 | 1.8 | 1.9 | 2.5 | 2.8 | 3.8 | 4.2 | 4.5 |

An advantage of using ATs is that they form reproducible SAMs and chemically defined surfaces. This attribute means that the surfaces created are chemically defined surfaces that will vary only because of the peptide or additional ligand(s) presented on the surface and not because of other bulk properties of the surface, such as topology. Another advantage of using ATs is that the peptide or additional ligand(s) can be engineered to be presented to the pluripotent cells in defined areas of the surface and that other areas of the surface (i.e., background areas) can be engineered to resist both solvents and cell presence. In contrast to the surfaces previously constructed for culture of cells, the components of the chemically defined surfaces described herein are fully characterized with known quantities of all ingredients.

Long-term culture of pluripotent cells on the chemically defined surfaces described herein typically will begin by chemically, enzymatically or mechanically dissociating confluent pluripotent cells from a surface, such as Matrigel® or MEFs, into clumps/aggregates or even single cells. In some cases, the surface will be one of the chemically defined surfaces described herein, e.g. when plating confluent cells onto a fresh chemically defined surface.

The clumps or aggregates or single cells then can be plated onto a chemically defined surface as described herein in a protein-free basal medium such as Dulbecco's Modified Eagle's Medium (DMEM)/F12 or mTeSR or even phosphate-buffered saline (PBS) or Hank's Balanced Salt Solution (HBSS) to minimize any non-specific adsorption of proteins from the medium. After about 1 hour, the medium can be replaced with a defined culture medium such as, e.g., mTeSR™1 supplemented with a kinase inhibitor.

As used herein, a "chemically defined medium," "defined culture medium" or "defined medium" means that the medium has known quantities of all ingredients. Typically, serum that is normally added to culture medium for cell culture is replaced by known quantities of serum components, such as, e.g., albumin, insulin, transferrin and possibly specific growth factors (i.e., basis fibroblast growth factor, transforming growth factor or platelet-derived growth factor). Defined medium (DM) is therefore serum-free. As used herein, "serum-free" means that a medium does not contain serum or serum replacement, or that it contains essentially no serum or serum replacement. As used herein, "essentially" means a de minimus or reduced amount (i.e., less than 5%) of a component, such as serum, may be present.

An example of a DM suitable for use herein is TeSR™. The full constituents and methods of use of TeSR™ are described in Ludwig et al. See, Ludwig T, et al., "Feeder-independent culture of human embryonic stem cells," Nat. Methods 3:637-646 (2006); and Ludwig T, et al., "Derivation of human embryonic stem cells in defined conditions," Nat. Biotechnol. 24:185-187 (2006), each of which is incorporated herein by reference as if set forth in its entirety. Other DM formulations suitable for use herein include, e.g., mTeSR™ (StemCell Technologies; Vancouver, British Columbia, Canada), X-Vivo (BioWhittaker, Walkersville, Md.) and StemPro® (Invitrogen; Carlsbad, Calif.).

Kinase inhibitors, such as ROCK inhibitors, are known to protect single cells and small aggregates of cells. See, e.g., US Patent Application Publication No. 2008/0171385, incorporated herein by reference as if set forth in its entirety; and Watanabe K, et al., "A ROCK inhibitor permits survival of dissociated human embryonic stem cells," Nat. Biotechnol. 25:681-686 (2007). ROCK inhibitors are shown below to significantly increase pluripotent cell survival on chemically defined surfaces. ROCK inhibitors suitable for use herein include, but are not limited to, (S)-(+)-2-methyl-1-[(4-methyl-5-isoquinolinyl)sulfonyl]homopiperazine dihydrochloride (informal name: H-1152), 1-(5-isoquinolinesulfonyl) piperazine hydrochloride (informal name: HA-100), 1-(5-isoquinolinesulfonyl)-2-methylpiperazine (informal name: H-7), 1-(5-isoquinolinesulfonyl)-3-methylpiperazine (informal name: iso H-7), N-2-(methylamino)ethyl-5-isoquinoline-sulfonamide dihydrochloride (informal name: H-8), N-(2-aminoethyl)-5-isoquinolinesulphonamide dihydrochloride (informal name: H-9), N-[2-p-bromo-cinnamylamino)ethyl]-5-isoquinolinesulfonamide dihydrochloride (informal name: H-89), N-(2-guanidinoethyl)-5-isoquinolinesulfonamide hydrochloride (informal name: HA-1004), 1-(5-isoquinolinesulfonyl) homopiperazine dihydrochloride (informal name: HA-1077), (S)-(+)-2-Methyl-4-glycyl-1-(4-methylisoquinolinyl-5-sulfonyl)homopiperazine dihydrochloride (informal name: glycyl H-1152) and (+)-(R)-trans-4-(1-aminoethyl)-N-(4-pyridyl)cyclohexanecarboxamide dihydrochloride (informal name: Y-27632). The kinase inhibitor can be provided at a concentration sufficiently high that the cells survive and remain attached to the surface. An inhibitor concentration between about 3 µM to about 10 µM can be suitable. At lower concentrations, or when no ROCK inhibitor is provided, undifferentiated cells typically detach, while differentiated cells remain attached to the defined surface.

The inventors have exploited the observation that undifferentiated but not differentiated cells require ROCK inhibitor for attachment to the chemically defined surfaces to separate differentiated from undifferentiated cells. For example, pluripotent or multipotent cells can be maintained on the chemically defined surfaces in the presence of ROCK inhibitor. At a desired time, the cells can be induced to differentiate on the chemically defined surfaces by, for example, adding one or more differentiation agent to the cell culture medium. Alternatively, pluripotent and non-pluripotent cells can be plated onto the chemically defined surfaces directly. To separate differentiated from undifferentiated cells, ROCK inhibitor is removed from the culture media, such that undifferentiated, but not differentiated, cells detach from the surface leaving behind a population of attached, differentiated cells.

During culture on the chemically defined surface, conventional cell culture conditions can be used. For example, the temperature can vary between about 36° C. to about 37.5° C. Likewise, the $CO_2$ concentration can, and will, vary between about 2% to about 10% depending on the medium and bicarbonate concentration. For example, the cell culture conditions can be 37° C. and 5% $CO_2$ in a humidified chamber. The pluripotent cells can be cultured to confluence (typically about 5 days to about 6 days), at which time, they can be passaged by methods known in the art (i.e., by chemical, enzymatic or mechanical means).

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

In describing the embodiments and claiming the invention, the following terminology will be used in accordance with the definitions set out below.

As used herein, "about" means within 5% of a stated concentration range, density, temperature, or time frame.

As used herein, "homologous" refers those polypeptides sharing at least 90% or at least 95% sequence identity to a given GBP (e.g., SEQ ID NOS:1-3) that result in binding by pluripotent cells via the cell surface. For example, a polypeptide that is at least 90% or at least 95% identical to the GBPs discussed herein is expected to be a constituent of a complex between the peptide and a molecule on the exterior surface of a pluripotent cell. One of ordinary skill in the art understands that modifications to the polypeptide can include substitutions, insertions (e.g., adding no more than ten amino acid) and deletions (e.g., deleting no more than ten amino acids).

These modifications can be introduced into the polypeptides discussed herein without abolishing structure and ultimately, function. Polypeptides containing such modifications can be used in the methods described herein.

In addition, it is well known in the art that amino acids within the same conservative group can typically substitute for one another without substantially affecting the function of a protein. For the purpose of the present invention, such conservative groups are set forth in Table 3 and are based on shared properties.

TABLE 3

Amino Acid Conservative Substitutions.

| Original Residue | Conservative Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

The gene and protein sequences for vitronectin, fibronectin and bone sialoprotein are known and characterized, see, e.g., GeneID numbers 7448, 2335, and 3381, respectively. All of the sequences defined by the above-noted GeneID numbers are incorporated by reference here in their entirety. Also, information about other GAG-binding molecules that can be used to support pluripotent stem cell self renewal is found, for example, in Fromm, J. R., et al., Pattern and Spacing of Basic Amino Acids in the Heparin Binding Sites, *Arch. Biochem. Biophys.* 343:92 (1997); which is incorporated by reference here in its entirety.

Each mentioned publication is incorporated by reference as if set forth herein in its entirety.

The invention will be more fully understood upon consideration of the following non-limiting Examples.

EXAMPLES

Example 1

Culture and Self-Renewal of hESCs and iPS Cells on Chemically Defined Surfaces Presenting GBPs Methods:
Cell Culture:
H1, H7, H9, H13, or H14 hESCs (WiCell Research Institute) and iPS cells (DF19-9 and IMR90-derived iPS cells) were maintained on Matrigel®-coated plates (Matrigel® obtained from BD Biosciences; Franklin Lakes, N.J.) using mTeSR™1 medium. The cells were maintained at 37° C. and 5% $CO_2$ and manually passaged every 5-6 days after treating with 2 mg/ml Dispase® (Gibco; Rockville, Md.) for 5-6 minutes.

hESCs were passaged to SAMs of peptide-AT conjugates on gold in mTeSR™1 optionally supplemented with 10 ng/ml heregulin-β1 (Peprotech; Rocky Hill, N.J.) and 5 μM Y-27632 (Calbiochem; San Diego, Calif.). The heregulin evidenced modest improvement of initial cell survival. Some surfaces presented peptide-AT conjugates of only vitronectin GBP (SEQ ID NO:1), fibronectin GBP (SEQ ID NO:2) or bone sialoprotein GBP (SEQ ID NO:3) Alternatively, some surfaces presented peptide-AT conjugates of only the integrin-binding peptide (SEQ ID NO:5), another bioactive peptide derived from fibronectin (SEQ ID NO:6), the FGF receptor binding peptide (SEQ ID NO:4), the laminin-derived bioactive peptide (SEQ ID NO:7), ADSQLIHGGLRS (SEQ ID NO: 8) or MHRMPSFLPTTL (SEQ ID NO: 9). Furthermore, some surfaces presented separate peptide-AT conjugates of the integrin-binding peptide (SEQ ID NO:5) and FGF receptor binding peptide (SEQ ID NO:4); the integrin-binding peptide (SEQ ID NO:5) and vitronectin GBP (SEQ ID NO:1); the integrin-binding peptide (SEQ ID NO:5) and bioactive peptide derived from fibronectin (SEQ ID NO:6); and the vitronectin GBP (SEQ ID NO:1) and MRHMPSFLPTTL (SEQ ID NO: 9). The density of the peptides on the surface varied from 0.5% to 25% (see, FIG. 1).

Moreover, some hESCs were passaged to streptavidin-coated plates treated with biotinylated vitronectin GBP (SEQ ID NO:1) or polyacrylamide gels cross-linked to vitronectin GBP (SEQ ID NO:1).

Regardless of the nature of the chemically defined surface or peptide(s) attached thereto, about $5 \times 10^4$ cells/ml were manually passaged to a fresh chemically defined surface every 5-7 days (i.e., at confluency) after treatment with an Enzyme-Free Cell Dissociation Buffer (Sigma; St. Louis, Mo.; a phosphate-buffered saline (PBS)+ethylenediamine tetraacetic acid (EDTA) 0.02% wt/vol) for 10-15 minutes. After three passages (about 21 days), the cells were evaluated for pluripotent cell-specific markers by flow cytometry.

Cell Adhesion:
To determine the effect of a soluble GAG on hESC binding to GBPs, hESCs were plated onto Matrigel-coated surfaces, vitronectin-coated surfaces, or surfaces presenting the heparin-binding peptide GKKQRFRHRNRKG (SEQ ID NO: 1) in the presence or absence of soluble heparin (0.5 mg/mL). After 1 hour, the surfaces were washed and the cells lysed. The cell lysates were used to determine approximate cell numbers using Cell Titer Glo (Promega). The ratio of the mean luminescence of the cell lysates of cells plated in the presence of heparin versus those without heparin was expressed as percent cell binding for each surface.

To determine if glycosaminoglycans (GAGs) are required for GBP binding, human ESCs (H9) cultured on Matrigel were dissociated using an enzyme-free, Hanks'-based cell dissociation buffer (Sigma) for 10-15 minutes. Cells were resuspended in DMEM/F12 (Gibco), or DMEM/F12 supplemented with 2 units/mL chondroitinase ABC (Sigma), or 500 ug/mL heparin (Sigma). Cells treated with the GAG-degrading enzymes were incubated for 1 hour in suspension at 37° C. Cell suspensions were seeded onto Matrigel-coated surfaces, recombinant vitronectin-coated surfaces (10 μg/mL, R&D Systems), or SAMs presenting the peptide GKKQRFRHRN-RKG (SEQ ID NO: 1) at a 5% surface density. After 1 hour, surfaces were washed 3 times with PBS and the cells were lysed with M-PER buffer (Thermo Fisher Scientific, Inc., Rockford, Ill.). The cell lysate was mixed with CellTiter-Glo (Promega) to determine the number of viable cells in culture based on the presence of ATP. The luminescence was measured on 20/20" luminometer (Turner Biosystems, Inc., Sunnyvale Calif.).

Cell Growth:

hESCs (H9) were cultured on Matrigel, vitronectin, polylysine, GKKQRFRHRNRKG (SEQ ID NO: 1), or KGRGDS (SEQ ID NO: 5) over two passages in mTeSR media supplemented with 5 μm ROCK inhibitor. Cell counts were calculated at each time point using Cell Counting Kit-8 (Dojindo Molecular Technologies, Inc., Rockville, Md.).

hESC Differentiation:

After culture for more than 3 months, hESCs were allowed to form embryoid bodies (EBs) in a suspension culture, which were formed in poly(2-hydroxyethyl methacrylate)-coated flasks (Greiner Bio-One; Monroe, N.C.), and cultured in a medium of Iscove's Modified Dulbecco's Medium (Gibco), 15% fetal bovine serum (FBS; Gibco), 1% non-essential amino acids (Gibco) and 0.1 mM β-mercaptoethanol (Gibco).

Microscopy and Immunostaining:

Images were collected with a Hamamatsu (Bridgewater, N.J.) Digital Camera mounted onto an Olympus IX81 Microscope. Primary antibodies used were as follows: Oct-4 (1:400; R&D Systems; Minneapolis, Minn.), SSEA-4 (1:400; Santa Cruz Biotechnology; Santa Cruz, Calif.), β-III tubulin (1:3000; R&D Systems), nestin (1:3000), α-fetoprotein (1:250; Sigma), FoxA2 (1:100; R&D Systems), α-smooth muscle actin (1:1000; Sigma), and fatty acid binding protein 4 (1:250; R&D Systems). Cells were fixed with PBS containing 4% formaldehyde and 0.15% picric acid for 20 minutes at 37° C. and then permeabilized and blocked with PBS containing 0.1% Triton X-100 and 0.1% bovine serum albumin (BSA). All antibodies were incubated in blocking buffer overnight at 4° C., except for the antibodies against β-III tubulin, nestin and α-smooth muscle actin, which were incubated for 1 hour at room temperature. Secondary staining was performed with Alexa Fluor® 488- and/or 594-conjugated antibodies (1:1000; Invitrogen) diluted in blocking buffer and incubated for 1 hour at room temperature. Cells were counterstained with 4',6-diamidino-2-phenylindole, dilactate (DAPI; Invitrogen). Image overlays were generated using ImageJ (ImageJ is a public domain Java image processing program available on the World Wide Web). Peptide array mosaics were generated using the AnalySIS Acquisition Software (Olympus).

Flow Cytometry:

hESCs were dissociated with 0.05% trypsin-EDTA with 2% chicken serum (Gibco). Cell surface marker staining was performed in PBS containing 2% BSA (wt/vol) at 4° C. for 30 minutes with directly conjugated antibodies against alkaline phosphatase (R&D Systems), Tra 1-60 (BD Biosciences), Tra 1-81 (BD Biosciences), SSEA-4 (BD Biosciences), SSEA-3 (BD Biosciences), SSEA-1 (R&D Systems) followed by a 30 minute fixation with 2% formaldehyde/PBS at room temperature.

For intracellular marker staining, hESCs were fixed with 2% formaldehyde/PBS at room temperature for 30 minutes. For Oct-4 staining, cells were permeabilized with saponin permeabilization buffer (SPB; 0.1% saponin, 0.1% BSA wt/vol in PBS) for 30 minutes at room temperature followed by incubation with an Oct-4 PE-conjugated antibody overnight. Cells were then washed 2 times with SPB before analysis.

For Sox-2 staining, cells were permeabilized with 90% ice-cold methanol, washed with SPB, incubated with Sox-2 Alexa-Fluor® conjugated antibody for 1 hour at 4° C., and then washed 2 times with SPB.

Flow cytometry data was obtained using a FACSCalibur™ (BD Biosciences) and analyzed using FlowJo Software (Tree Star, Inc.; Ashland, Oreg.). The percentage of positive cells was established by comparing experimental cells to partially differentiated hESCs. Gating for positive and negative populations was established by analyzing the bimodal peaks of partially differentiated hESCs.

G-Banded Karyotyping:

Human ES cells were harvested as follows. Ethidium bromide (0.001% final concentration; ThermoFisher Scientific, http://www.thermofisher.com, Waltham, Mass.) was added directly to actively dividing cultures (day 3 or 4 after passage) that were then incubated for 40 minutes in a 37° C. incubator with 5% $CO_2$. Colcemid (200 ng/ml final concentration; Invitrogen) was added to the cultures, and they were returned to the incubator for an additional 30 minutes. Cells were disassociated with 0.05% trypsin-EDTA (Invitrogen), centrifuged, resuspended in 5 ml of 0.075M KCl hypotonic (Invitrogen), and incubated in a 37° C. waterbath for 18-25 minutes. Cell suspensions were pre-fixed for five minutes at room temperature with 20 drops of 3:1 methanol to acetic acid fixative (low water methanol, certified ACS plus acetic acid; ThermoFisher Scientific). Following centrifugation (200×g for 5 min), the pre-fixation solution was removed, replaced with fixative, and incubated at room temperature for 30 min. Fixative was replaced at least 2 more times. Fixed cell suspensions were dropped onto glass slides under controlled temperature and humidity conditions (25° C./33% humidity) in a CDS-5 Cytogenetics Drying Chamber (Thermotron, Holland, Mich., http://www.thermotron.com). These preparations were heated for 1 hour at 90° C. on a ThermoBrite StatSpin (Abbott) to "age" the metaphase spreads for G-banding and allowed to cool to room temperature. Slides were dipped in 1× trypsin-EDTA (0.05%, diluted in HBSS (Invitrogen)) for 25-30 seconds followed by brief washes in a FBS solution (2% (v/v), Invitrogen, diluted in HBSS) and MilliQ water (Millipore). Chromosomes were stained for 90 seconds with Leishman's stain (0.2% (w/v), Sigma, dissolved in methanol (Fisher)) diluted 1:4 in Gurr buffer (Invitrogen), followed by two brief washes in MilliQ water (Millipore). The slides were dried on a 50° C. hotplate for 15 min and coverslipped with Cytoseal-60 mounting media (Richard-Allan Scientific, Kalamazoo, Mich., http://www.rallansci.com). G-Band analysis was performed by random selection of at least 20 metaphases. Chromosomes in each selected metaphase cell were counted to establish modal chromosome number, a minimum of 8 were analyzed microscopically, and at least 4 of these were karyogrammed. Metaphase images were captured and analyzed with the Applied Spectral Imaging (ASI) acquisition and BandView software (Vista, Calif., http://www.spectral-imaging.com) with an Olympus BX41 microscope (Olympus, Center Valley, Pa., http://www.olympusamerica.com).

Defined Surface Fabrication:

Chromium (1 nm) and then gold (25 nm) were evaporated onto piranha solution-cleaned glass coverslips (Corning No 1½ A, 23 mm squares) using a thermal evaporator (Denton Vacuum; Moorestown, N.J.). Substrates were immediately immersed into a 1 mM solution of fluoro-AT in absolute ethanol. After 24 hours, substrates were thoroughly rinsed with ethanol and dried under a stream of nitrogen. Coverslips with fluoro-AT SAM were irradiated with UV-light (1 kW—Hg—Xe Research Arc Lamp; Spectra-Physics; Stratford, Conn.) through a quartz photomask (array of 500 μm or 750 μm squares, 0.067 quartz-chromium mask (Photo Sciences, Torrance, Calif.)) for 1 hour. Irradiated samples were rinsed thoroughly using several repetitive washes with absolute ethanol and distilled water and dried under a stream of nitrogen.

Spotting of AT solutions onto the bare gold areas was performed within 2 hours of the photolithography. Spotting was performed manually using a P2-Pipetman (Gilson; Middleton, Wis.) in a humidity chamber. Spotted arrays were stored in the humidity chamber for 12 hours and thoroughly washed using repeated washes with ethanol and water. Rapid flow during washing was used to prevent cross-contamination of array spots.

Alternatively, glass slides coated with 250 Å Gold and 10 Å Chromium, 22 mm square, 0.16 mm thick) were purchased from EMF Corporation. Arrays were prepared as previously described. Derda, R. et al., "Defined substrates for human embryonic stem cell growth identified from surface arrays," ACS Chem. Biol. 2, 347-355 (2007), incorporated herein by reference as if set forth in its entirety. When larger areas of peptide-AT SAMs were needed, whole chips presenting the same SAM were fabricated by sandwiching solutions of peptide-AT/glucamine-AT between two gold coated slides. SAMs were allowed to form in humidity chambers for 24 h before use.

Peptide-ATs:

Peptides were synthesized on a Pioneer™ Peptide Synthesis System (Applied Biosystems; Foster City, Calif.) using standard Fmoc chemistry on Rink Amide AM Resin (Novabiochem; loading: 0.56 mmol/g). Peptide-AT conjugates were prepared similarly to Houseman & Mrksich, supra. Briefly, resin containing protected peptide with a free N-terminus was swollen in dry THF, 5-fold excess of each of the compound 1, HOBt and 1,3-diisopropylcarbodiimide (DIC) was added to the resin suspension in THF. The resin was incubated for 12 hours and another 3-fold excess of DIC and HOBt was added. After 3 hours, the resin was tested with the Kaiser Test (see, Kaiser E, et al., "Color test for detection of free terminal amino groups in solid-phase synthesis of peptides," Anal. Biochem. 34:595-598 (1970)), washed with DMF and dichloromethane and dried in vacuo. After cleavage with TFA/DIC/EDT/H$_2$O/phenol (36:1:1:1:1) for 2 hours and ether precipitation, conjugates were purified by preparative HPLC. Gradient used (percentage of mobile phase A): 100→0% 20 min, 0% 3 min. 0→100% 3 minutes. Peaks at retention time around 17 minutes were collected. Each purified sample was analyzed by LCMS and H NMR. Note: The presence of triplet of 1,1,1-triples δ 2.49 (t[111t], 2H, J=7.1 Hz, J$_{HD}$=1.0 Hz) in H NMR at AT-peptides in CD$_3$OD is indicative of free thiol functionality. It is the signal of methylene hydrogens next to the free thiol functionality (7 NZ, coupling to neighboring methylene, 1 Hz coupling to deuterium on free thiol).

Figure 2:
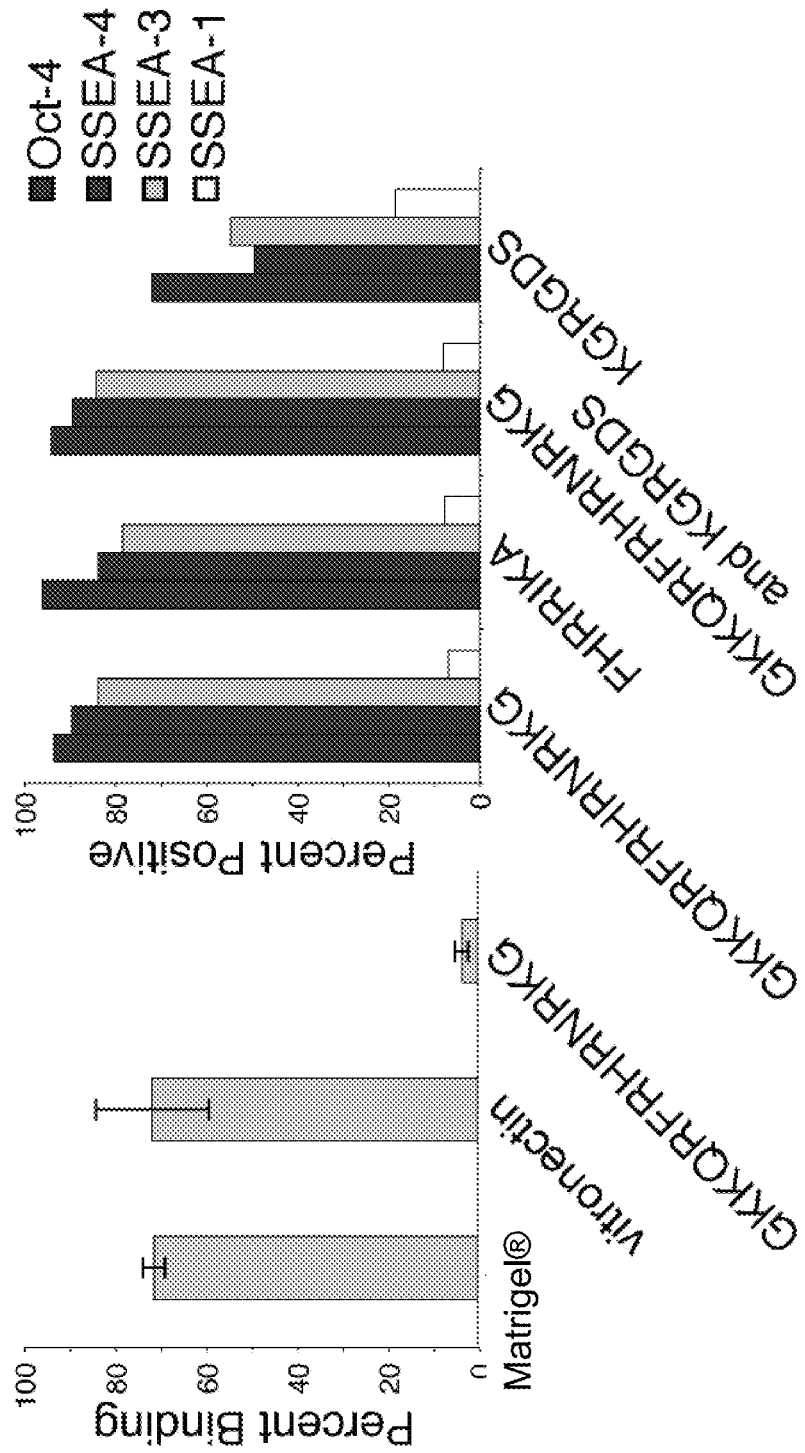
FIG. 2 shows that GBPs support pluripotent cell self-renewal over at least several passages.

Results:

The inventors examined whether GBPs, such as SEQ ID NO:1, alone or in combination with other adhesion peptides could support pluripotent cell attachment, growth, and maintenance using alternative methods of presentation. The chemically defined surfaces described herein showed excellent attachment, self-renewal, and colony spreading, but required a certain degree of chemical expertise to produce.

hESCs (H1 and H9) propagated in mTeSR media supplemented with Y-27632, an inhibitor of Rho-associated coiled-coiled kinase (ROCK), on surfaces presenting GBPs for 6 days maintained high levels of Oct-4 and SSEA-4 expression (FIG. 1). Cells treated with a glycosaminoglycan-degrading chondroitinase ABC enzyme maintained their ability to adhere to Matrigel and vitronectin but exhibited decreased adhesion to the synthetic surfaces presenting GKKQRFRHRNKG (SEQ ID NO: 1). Soluble heparin, which competed with cell surface GAGs for binding to the surface, also inhibited adhesion (FIG. 2A).

A variety of peptidic surfaces supported hESC attachment, growth, and maintenance. Interestingly, peptide surfaces presenting GBP, like vitronectin GBP, best supported both cell attachment and self-renewal, as determined by the presence of Oct-4 and SSEA-4 after 6 days. Notably, while a combination of RGD peptides and vitronectin GBP supported cell self-renewal, integrin binding through RGD peptides was not necessary for self-renewal (see, FIG. 2).

RGD-presenting surfaces are inferior substrata for pluripotent stem cell propagation. Cells cultured on GBPs displayed a high nucleus to cytoplasm ratio, maintained high levels of markers of pluripotency (FIG. 2B), and grew in the form of tightly packed colonies characteristic of undifferentiated hES cells. In contrast, cell populations grown on RGD-presenting surfaces grew in the form of heterogeneous mixtures of colonies and individual cells, and fewer cells in the population displayed markers of pluripotency (FIG. 2B). Consistently, cells cultured on RGD-presenting surfaces exhibited a variety of morphologies and differentiated into all three embryonic germ layers. Thus, attachment to RGD peptides alone was insufficient to support self-renewal.

Figure 3B:
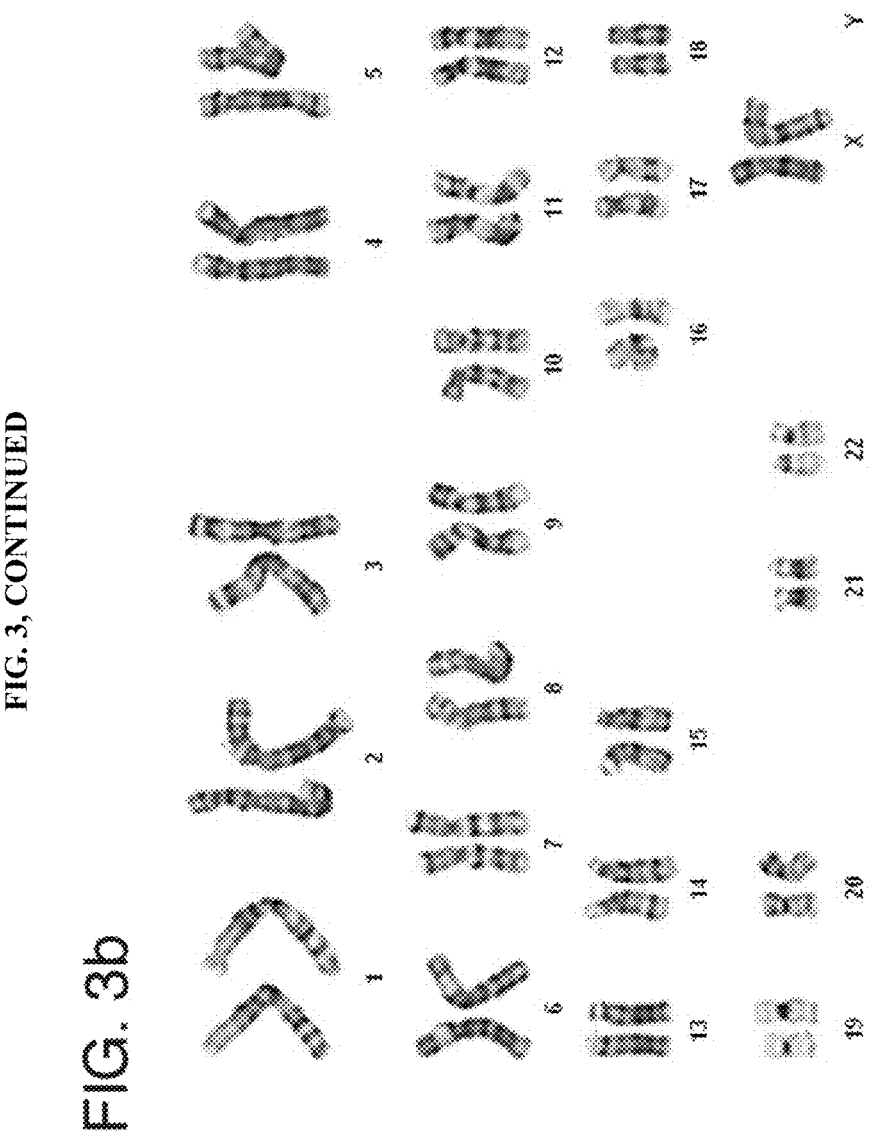

After 3 months of continuous passaging on defined surfaces presenting SEQ ID NO:1, cells were evaluated for pluripotent cell-specific markers such as Oct-4 and SSEA-4 (see, FIG. 3B), NANOG and SOX2, which were maintained at high levels. Importantly, cells cultured on GBP-presenting surfaces formed homogenous populations of undifferentiated pluripotent cells (FIG. 3A) that grew in densely packed colonies. In contrast, cells cultured on Matrigel® formed heterogeneous cell populations. While gene expression levels of markers associated with pluripotency were comparable between cells grown on Matrigel and cells grown on GBP-presenting surfaces, cells grown on Matrigel lost cell surface expression of certain pluripotency markers (FIG. 3A). In contrast, cells grown on GBP-presenting surfaces maintained cell-surface expression of these markers. Furthermore, cells cultured on GBP-presenting surfaces remained karyotypically normal over the course of the experiment (see, FIG. 3B).

GBP-presenting surfaces are superior to polylysine-coated surfaces in promoting cell divisions. The growth characteristics of pluripotent stem cells cultured on standard substrata were compared to those of cells cultured on surfaces presenting synthetic peptides. Growth curves were generated for hES cells (H9 and H13) and vector-free iPS cells (DF19-9) cultured on various surfaces over two passages. Matrigel-coated surfaces exhibited a slightly higher plating efficiency after 24 hours compared to vitronectin- and GKKQRFRHRNKG (SEQ ID NO: 1)-coated surfaces, which were equivalent. Surfaces presenting the synthetic peptide KGRGDS (SEQ ID NO: 5) had the lowest plating efficiency (FIG. 5). Increased cell numbers were observed after each passage for cells cultured on Matrigel-coated, vitronectin-coated, and GKKQR-FRHRNKG (SEQ ID NO: 1)-presenting surfaces (FIG. 5).

Cells cultured on synthetic surfaces presenting the heparin-binding peptide GKKQRFRHRNKG (SEQ ID NO: 1) or a combination of GKKQRFRHRNKG (SEQ ID NO: 1) and KGRGDS (SEQ ID NO: 5) underwent a similar number of cell divisions as cells cultured on Matrigel, as indicated by fluorescent cell staining. In contrast, cells cultured on vitronectin-coated surfaces and synthetic surfaces presenting KGRGDS (SEQ ID NO: 5) underwent fewer cell divisions. Importantly, GKKQRFRHRNKG(SEQ ID NO: 1)-presenting surfaces are superior to polylysine-coated surfaces in promoting cell divisions.

Other chemically defined surfaces in addition to SAMs were also suitable for culture of pluripotent cells. For example, streptavidin-coated plates treated with biotinylated SEQ ID NO:1 supported cell adhesion and growth, although not to the same extent as when SEQ ID NO:1 was presented on SAMs (data not shown). Interestingly, colony spreading was lower than on SAMs but ROCK inhibitor can be omitted without observable increase in cell death, suggesting that other peptide-presenting scaffolds might not need ROCK inhibitor in the culture medium. Likewise, CGKKQR-FRHRNRKG (SEQ ID NO: 47) conjugated to polyacrylamide gels or glass coverslips supported cell adhesion and growth comparable to SAMs. These results demonstrate that a variety of substrates that display GAG-binding peptides can sustain pluripotent cell adhesion and growth.

Pluripotent cells cultured on the chemically defined, peptide-presenting surfaces retained not only their ability to self-renew, but also their ability to differentiate into cells from the three germ layers. After culture on chemically defined surfaces presenting SEQ ID NO:1 for 3 months, the cells subsequently formed EBs in a suspension culture. After 2 weeks in the suspension culture, a heterogeneous population of cells was stained for markers of all 3 embryonic germ layers, and stained positive for 13-III tubulin and nestin, indicating derivatives of the ectoderm. In addition, some cells stained positive for fatty acid binding protein 4 and α-smooth muscle actin, indicating derivatives of the mesoderm. Finally, some cells stained positive for α-fetoprotein and FoxA2, indicating derivatives of the endoderm. Similar results were obtained using several hESC lines (e.g., H1, H7, H9, and H13) cultured on the synthetic substrate for 1 month (6 passages).

Example 2

Separation of Pluripotent from Nonpluripotent Cells Cultured on Chemically Defined Surfaces Presenting GBPs Methods:

GBP-presenting surfaces were produced essentially as described in Example 1. Pluripotent cells were cultured essentially as described in Example 1.

Effect of ROCK inhibitor on cellular adhesion: A mixture of undifferentiated hESCs (Oct-4 positive) and differentiated cells derived from embryoid bodies (Oct-4 negative) was seeded onto self-assembled monolayer surfaces presenting the GBP GKKQRFRHRNRKG (SEQ ID NO: 1) and the integrin binding peptide KGRGDS (SEQ ID NO: 5). For some experiments, cells were seeded onto polyacrylamide gels or glass coverslips presenting the CGKKQRFRHRN-RKG (SEQ ID NO: 47) peptide. The cells were grown for 24 hours in mTeSR medium containing 5 µM ROCK inhibitor Y-27632 and then switched to mTeSR medium without ROCK inhibitor for an additional 24 hours. The cells were fixed and stained for Oct-4 and counterstained with phalloidin and DAPI. In some instances, cells were added to the surfaces without ROCK inhibitor.

Results:

As described in Example 1, pluripotent cells cultured on surfaces presenting GBPs in the presence of the ROCK inhibitor maintained high levels of pluripotent cell-specific markers (FIG. 2B). However, significant detachment of undifferentiated cells was observed after removal of the ROCK inhibitor. In contrast, differentiated cells remained attached and viable after the removal of ROCK inhibitor. Thus, removal of the ROCK inhibitor from the media selectively detached undifferentiated, potentially teratoma-forming cells leaving a population of differentiated cells. When cells were added to the surfaces without the ROCK inhibitor, some cells adhered to the surfaces but few of these cells were Oct-4 positive undifferentiated cells.

In summary, the experiments described herein demonstrate that chemically defined, peptide-presenting surfaces having as little as a single type of peptide can be used for routine culture and self-renewal of pluripotent cells. In particular, SAMs presenting the peptides described herein provided attachment, self-renewal, and colony spreading.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A composition comprising:
   an insoluble substrate having a surface that presents a GAG-binding peptide selected from the group consisting of SEQ ID NO:1 and SEQ ID NO:2;
   a culture medium that supports growth of pluripotent stem cells; and
   pluripotent stem cells adhering to the surface, wherein the cells display pluripotent cell-specific markers and an ability to differentiate into all three germ layers after more than three months of adhering to the surface.

2. The composition as recited in claim 1, wherein the culture medium comprises a ROCK kinase inhibitor.

3. The composition as recited in claim 1, wherein adhering to the surface comprises binding to surface-presented GAG binding peptides.

4. The composition as recited in claim 1, wherein the culture medium is a chemically defined medium.

5. The composition as recited in claim 2, wherein the ROCK kinase inhibitor is selected from the group consisting of (S)-(+)-2-methyl-1-[(4-methyl-5-isoquinolinyl)sulfonyl]homopiperazine dihydrochloride (H-1152), 1-(5-isoquinolinesulfonyl)piperazine hydrochloride (informal name: HA-100), 1-(5-isoquinolinesulfonyl)-2-methylpiperazine (H-7), 1-(5-isoquinolinesulfonyl)-3-methylpiperazine (iso H-7), N-2-(methylamino)ethyl-5-isoquinoline-sulfonamide dihydrochloride (H-8), N-(2-aminoethyl)-5-isoquinoline-sulphonamide dihydrochloride (informal name: H-9), N-[2-p-bromo-cinnamylamino)ethyl]-5-isoquinolinesulfonamide dihydrochloride (H-89), N-(2-guanidinoethyl)-5-isoquinolinesulfonamide hydrochloride (HA-1004), 1-(5-isoquinolinesulfonyl) homopiperazine dihydrochloride (HA-1077), (S)-(+)-2-Methyl-4-glycyl-1-(4-methylisoquinolinyl-5-sulfonyl)homopiperazine dihydrochloride (glycyl H-1152), and (+)-(R)-trans-4-(1-aminoethyl)-N-(4-pyridyl)cyclohexanecarboxamide dihydrochloride (Y-27632).

\* \* \* \* \*

SEQUENCE LISTING

```
<160> NUMBER OF SEQ ID NOS: 48

<210> SEQ ID NO 1
<211> LENGTH: 13
<212> TYPE: PRT
<213> ORGANISM: Homo sapiens

<400> SEQUENCE: 1

Gly Lys Lys Gln Arg Phe Arg His Arg Asn Arg Lys Gly
1               5                   10

<210> SEQ ID NO 2
<211> LENGTH: 9
<212> TYPE: PRT
<213> ORGANISM: Homo sapiens

<400> SEQUENCE: 2

Gly Trp Gln Pro Pro Arg Ala Arg Ile
1               5

<210> SEQ ID NO 3
<211> LENGTH: 7
```

```
<212> TYPE: PRT
<213> ORGANISM: Homo sapiens

<400> SEQUENCE: 3

Phe His Arg Arg Ile Lys Ala
1               5

<210> SEQ ID NO 4
<211> LENGTH: 18
<212> TYPE: PRT
<213> ORGANISM: Homo sapiens

<400> SEQUENCE: 4

Gly Gly Gly Glu Val Tyr Val Val Ala Glu Asn Gln Gln Gly Lys Ser
1               5                   10                  15

Lys Ala

<210> SEQ ID NO 5
<211> LENGTH: 6
<212> TYPE: PRT
<213> ORGANISM: Homo sapiens

<400> SEQUENCE: 5

Lys Gly Arg Gly Asp Ser
1               5

<210> SEQ ID NO 6
<211> LENGTH: 6
<212> TYPE: PRT
<213> ORGANISM: Homo sapiens

<400> SEQUENCE: 6

Lys Pro His Ser Arg Asn
1               5

<210> SEQ ID NO 7
<211> LENGTH: 10
<212> TYPE: PRT
<213> ORGANISM: Homo sapiens

<400> SEQUENCE: 7

Gly Ser Asp Pro Gly Tyr Ile Gly Ser Arg
1               5                   10

<210> SEQ ID NO 8
<211> LENGTH: 12
<212> TYPE: PRT
<213> ORGANISM: Homo sapiens

<400> SEQUENCE: 8

Ala Asp Ser Gln Leu Ile His Gly Gly Leu Arg Ser
1               5                   10

<210> SEQ ID NO 9
<211> LENGTH: 12
<212> TYPE: PRT
<213> ORGANISM: Homo sapiens

<400> SEQUENCE: 9

Met His Arg Met Pro Ser Phe Leu Pro Thr Thr Leu
1               5                   10

<210> SEQ ID NO 10
<211> LENGTH: 28
```

```
<212> TYPE: PRT
<213> ORGANISM: Homo sapiens

<400> SEQUENCE: 10

Phe Phe Phe Glu Arg Leu Glu Ser Asn Asn Tyr Asn Thr Tyr Arg Ser
1               5                   10                  15

Arg Lys Tyr Ser Ser Trp Tyr Val Ala Leu Lys Arg
            20                  25

<210> SEQ ID NO 11
<211> LENGTH: 27
<212> TYPE: PRT
<213> ORGANISM: Homo sapiens

<400> SEQUENCE: 11

Pro Asn Gly Leu Lys Arg Asp Lys Leu Gly Cys Glu Tyr Cys Glu Cys
1               5                   10                  15

Arg Pro Lys Arg Lys Leu Ile Pro Arg Leu Ser
            20                  25

<210> SEQ ID NO 12
<211> LENGTH: 8
<212> TYPE: PRT
<213> ORGANISM: Homo sapiens

<400> SEQUENCE: 12

Leu Arg Lys Arg Leu Leu Arg Asp
1               5

<210> SEQ ID NO 13
<211> LENGTH: 8
<212> TYPE: PRT
<213> ORGANISM: Homo sapiens

<400> SEQUENCE: 13

Gly Glu Arg Leu Arg Ala Arg Met
1               5

<210> SEQ ID NO 14
<211> LENGTH: 19
<212> TYPE: PRT
<213> ORGANISM: Homo sapiens

<400> SEQUENCE: 14

Arg Lys Asn Arg Cys Asn Asn Leu Gly Tyr Glu Ile Asn Lys Val Arg
1               5                   10                  15

Ala Lys Arg

<210> SEQ ID NO 15
<211> LENGTH: 18
<212> TYPE: PRT
<213> ORGANISM: Homo sapiens

<400> SEQUENCE: 15

Arg Glu His Ser Glu Arg Lys Lys Arg Arg Glu Ser Glu Cys Lys
1               5                   10                  15

Ala Ala

<210> SEQ ID NO 16
<211> LENGTH: 23
<212> TYPE: PRT
<213> ORGANISM: Homo sapiens
```

```
<400> SEQUENCE: 16

Tyr Ile Gly Leu Lys Asp Arg Lys Arg Pro Ser Glu Leu Arg Arg Ile
1               5                   10                  15

Ala Ser Gln Val Lys Tyr Ala
            20

<210> SEQ ID NO 17
<211> LENGTH: 18
<212> TYPE: PRT
<213> ORGANISM: Homo sapiens

<400> SEQUENCE: 17

Thr Trp Lys His Lys Gly Arg Asp Val Ile Leu Lys Lys Asp Val Arg
1               5                   10                  15

Phe Ile

<210> SEQ ID NO 18
<211> LENGTH: 37
<212> TYPE: PRT
<213> ORGANISM: Homo sapiens

<400> SEQUENCE: 18

Arg Arg Ala Arg Val Thr Asp Ala Thr Glu Thr Thr Ile Thr Ile Ser
1               5                   10                  15

Trp Arg Thr Lys Glu Thr Glu Thr Ile Thr Gly Phe Gln Val Asp Ala
            20                  25                  30

Ile Pro Ala Asn Gly
        35

<210> SEQ ID NO 19
<211> LENGTH: 19
<212> TYPE: PRT
<213> ORGANISM: Homo sapiens

<400> SEQUENCE: 19

Tyr Glu Lys Pro Gly Ser Pro Pro Arg Glu Val Val Pro Arg Pro Arg
1               5                   10                  15

Pro Gly Val

<210> SEQ ID NO 20
<211> LENGTH: 15
<212> TYPE: PRT
<213> ORGANISM: Homo sapiens

<400> SEQUENCE: 20

Lys Asn Asn Gln Lys Ser Glu Pro Leu Ile Gly Arg Lys Lys Thr
1               5                   10                  15

<210> SEQ ID NO 21
<211> LENGTH: 20
<212> TYPE: PRT
<213> ORGANISM: Homo sapiens

<400> SEQUENCE: 21

Arg Tyr Val Val Leu Pro Arg Pro Val Cys Phe Glu Lys Gly Met Asn
1               5                   10                  15

Tyr Thr Val Arg
            20

<210> SEQ ID NO 22
<211> LENGTH: 17
```

```
<212> TYPE: PRT
<213> ORGANISM: Homo sapiens

<400> SEQUENCE: 22

Arg Ile Gln Asn Leu Leu Lys Ile Thr Asn Leu Arg Ile Lys Phe Val
1               5                   10                  15

Lys

<210> SEQ ID NO 23
<211> LENGTH: 22
<212> TYPE: PRT
<213> ORGANISM: Homo sapiens

<400> SEQUENCE: 23

Lys Gln Asn Cys Leu Ser Ser Arg Ala Ser Phe Arg Gly Cys Val Arg
1               5                   10                  15

Asn Leu Arg Leu Ser Arg
            20

<210> SEQ ID NO 24
<211> LENGTH: 15
<212> TYPE: PRT
<213> ORGANISM: Homo sapiens

<400> SEQUENCE: 24

Ala Lys Lys Gln Arg Phe Arg His Arg Asn Arg Lys Gly Tyr Arg
1               5                   10                  15

<210> SEQ ID NO 25
<211> LENGTH: 22
<212> TYPE: PRT
<213> ORGANISM: Homo sapiens

<400> SEQUENCE: 25

Ala Lys Leu Asn Cys Arg Leu Tyr Arg Lys Ala Asn Lys Ser Ser Lys
1               5                   10                  15

Leu Val Ser Ala Asn Arg
            20

<210> SEQ ID NO 26
<211> LENGTH: 25
<212> TYPE: PRT
<213> ORGANISM: Homo sapiens

<400> SEQUENCE: 26

Lys Asp Gly Arg Lys Ile Cys Leu Asp Leu Gln Ala Pro Leu Tyr Lys
1               5                   10                  15

Lys Ile Ile Lys Lys Leu Leu Glu Ser
            20                  25

<210> SEQ ID NO 27
<211> LENGTH: 10
<212> TYPE: PRT
<213> ORGANISM: Homo sapiens

<400> SEQUENCE: 27

Lys Gly Lys Met His Lys Thr Cys Tyr Tyr
1               5                   10

<210> SEQ ID NO 28
<211> LENGTH: 10
<212> TYPE: PRT
<213> ORGANISM: Homo sapiens
```

```
<400> SEQUENCE: 28

Met Gly Lys Met His Lys Thr Cys Tyr Asn
1               5                   10

<210> SEQ ID NO 29
<211> LENGTH: 21
<212> TYPE: PRT
<213> ORGANISM: Homo sapiens

<400> SEQUENCE: 29

Lys Lys His Glu Ala Lys Asn Trp Phe Val Gly Leu Lys Lys Gly Ser
1               5                   10                  15

Cys Lys Arg Gly Pro
            20

<210> SEQ ID NO 30
<211> LENGTH: 20
<212> TYPE: PRT
<213> ORGANISM: Homo sapiens

<400> SEQUENCE: 30

Ser Glu Lys Thr Leu Arg Lys Trp Leu Lys Met Phe Lys Lys Arg Gln
1               5                   10                  15

Leu Glu Leu Tyr
            20

<210> SEQ ID NO 31
<211> LENGTH: 4
<212> TYPE: PRT
<213> ORGANISM: Homo sapiens

<400> SEQUENCE: 31

Leu Tyr Val Arg
1

<210> SEQ ID NO 32
<211> LENGTH: 4
<212> TYPE: PRT
<213> ORGANISM: Homo sapiens

<400> SEQUENCE: 32

Leu Arg Gln Lys
1

<210> SEQ ID NO 33
<211> LENGTH: 10
<212> TYPE: PRT
<213> ORGANISM: Homo sapiens

<400> SEQUENCE: 33

Arg Lys Gly Ser Gly Arg Arg Leu Val Lys
1               5                   10

<210> SEQ ID NO 34
<211> LENGTH: 7
<212> TYPE: PRT
<213> ORGANISM: Homo sapiens

<400> SEQUENCE: 34

Arg Gln Met Lys Lys Thr Arg
1               5
```

-continued

<210> SEQ ID NO 35
<211> LENGTH: 19
<212> TYPE: PRT
<213> ORGANISM: Homo sapiens

<400> SEQUENCE: 35

Asp Phe Arg Lys Asp Leu Gly Trp Lys Trp Ile His Glu Pro Lys Gly
1               5                   10                  15

Tyr His Ala

<210> SEQ ID NO 36
<211> LENGTH: 16
<212> TYPE: PRT
<213> ORGANISM: Homo sapiens

<400> SEQUENCE: 36

Leu Ser Val Lys Ala Gln Tyr Lys Lys Asn Lys His Arg His Ser Ile
1               5                   10                  15

<210> SEQ ID NO 37
<211> LENGTH: 20
<212> TYPE: PRT
<213> ORGANISM: Homo sapiens

<400> SEQUENCE: 37

Tyr Lys Leu Glu Gly Thr Thr Arg Leu Thr Arg Lys Arg Gly Leu Lys
1               5                   10                  15

Leu Ala Thr Ala
            20

<210> SEQ ID NO 38
<211> LENGTH: 18
<212> TYPE: PRT
<213> ORGANISM: Homo sapiens

<400> SEQUENCE: 38

Gly Arg Pro Arg Glu Ser Gly Lys Lys Arg Lys Arg Lys Arg Leu Lys
1               5                   10                  15

Pro Thr

<210> SEQ ID NO 39
<211> LENGTH: 15
<212> TYPE: PRT
<213> ORGANISM: Homo sapiens

<400> SEQUENCE: 39

Leu Gly Val Pro Ala Asn Arg Ile Val Val Arg Val Lys Arg Met
1               5                   10                  15

<210> SEQ ID NO 40
<211> LENGTH: 17
<212> TYPE: PRT
<213> ORGANISM: Homo sapiens

<400> SEQUENCE: 40

Lys Lys Lys Asn Pro Ser Gly Ser Trp Glu Asp Trp Val Thr Ala Ala
1               5                   10                  15

Tyr

<210> SEQ ID NO 41
<211> LENGTH: 24
<212> TYPE: PRT
<213> ORGANISM: Homo sapiens -continued

<400> SEQUENCE: 41

Arg Tyr Asn Val Asn Gly Val Gly Lys Val Leu Lys Lys Ile Asn Lys
1               5                   10                  15

Ala Ile Val Ser Lys Lys Asn Lys
            20

<210> SEQ ID NO 42
<211> LENGTH: 32
<212> TYPE: PRT
<213> ORGANISM: Homo sapiens

<400> SEQUENCE: 42

Gly Lys Cys Arg Pro Phe Lys Tyr Ser Gly Cys Gly Gly Asn Glu Asn
1               5                   10                  15

Asn Phe Thr Ser Lys Gln Glu Cys Leu Arg Ala Cys Lys Lys Gly Phe
            20                  25                  30

<210> SEQ ID NO 43
<211> LENGTH: 12
<212> TYPE: PRT
<213> ORGANISM: Homo sapiens

<400> SEQUENCE: 43

Arg Arg Leu Arg Arg Met Glu Ser Glu Ser Glu Ser
1               5                   10

<210> SEQ ID NO 44
<211> LENGTH: 18
<212> TYPE: PRT
<213> ORGANISM: Homo sapiens

<400> SEQUENCE: 44

Arg Lys Gly Phe Tyr Lys Arg Lys Gln Cys Lys Pro Ser Arg Gly Arg
1               5                   10                  15

Lys Arg

<210> SEQ ID NO 45
<211> LENGTH: 18
<212> TYPE: PRT
<213> ORGANISM: Homo sapiens

<400> SEQUENCE: 45

Lys Lys Gly Phe Tyr Lys Lys Lys Gln Cys Arg Pro Ser Lys Gly Arg
1               5                   10                  15

Lys Arg

<210> SEQ ID NO 46
<211> LENGTH: 21
<212> TYPE: PRT
<213> ORGANISM: Homo sapiens

<400> SEQUENCE: 46

Lys Arg Lys Lys Lys Gly Lys Gly Leu Gly Lys Lys Arg Asp Pro Cys
1               5                   10                  15

Leu Arg Lys Tyr Lys
            20

<210> SEQ ID NO 47
<211> LENGTH: 14
<212> TYPE: PRT
<213> ORGANISM: Homo sapiens

```
<400> SEQUENCE: 47

Cys Gly Lys Lys Gln Arg Phe Arg His Arg Asn Arg Lys Gly
1               5                   10

<210> SEQ ID NO 48
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be Lys, Arg or His
<220> FEATURE:
<221> NAME/KEY: MISC_FEATURE
<222> LOCATION: (2)..(3)
<223> OTHER INFORMATION: Xaa can be Ile, Val, Leu, Phe, Pro, Met or Ala
<220> FEATURE:
<221> NAME/KEY: MISC_FEATURE
<222> LOCATION: (4)..(4)
<223> OTHER INFORMATION: Xaa can be Lys, Arg or His

<400> SEQUENCE: 48

Xaa Xaa Xaa Xaa
1
```